United States Patent [19]

Brickl et al.

[11] 4,327,114
[45] Apr. 27, 1982

[54] SUBSTITUTED 1,8-DIHYDROXY-9-(10H)ANTHRACENONES

[75] Inventors: Rolf Brickl, Warthausen; Hans Eberhardt, Biberach, both of Fed. Rep. of Germany

[73] Assignee: Boehringer Ingelheim GmbH, Ingelheim am Rhein, Fed. Rep. of Germany

[21] Appl. No.: 223,335

[22] Filed: Jan. 8, 1981

[30] Foreign Application Priority Data

Jan. 22, 1980 [DE] Fed. Rep. of Germany ....... 3002089

[51] Int. Cl.³ .................. A61K 31/12; C07C 50/34
[52] U.S. Cl. .................................. 424/331; 260/351
[58] Field of Search ................... 568/326; 424/331; 260/351

[56] References Cited

U.S. PATENT DOCUMENTS

| | | | |
|---|---|---|---|
| 2,929,825 | 3/1960 | Stephens | 260/351 |
| 3,515,731 | 6/1970 | Conover | 260/351 |
| 3,538,126 | 11/1970 | Lange et al. | 260/351 |
| 3,947,594 | 3/1976 | Randall | 424/331 |
| 4,007,271 | 2/1977 | Robertson | 260/351 |

FOREIGN PATENT DOCUMENTS 283418 10/1952 Switzerland .................. 260/351

OTHER PUBLICATIONS

Mustakallia, Acta Dermatovener, vol. 59, #85, p. 125, (1979).

*Primary Examiner*—Natalie Trousof
*Assistant Examiner*—James H. Reamer
*Attorney, Agent, or Firm*—Hammond & Littell, Weissenberger & Muserlian

[57] ABSTRACT

Compounds of the formula

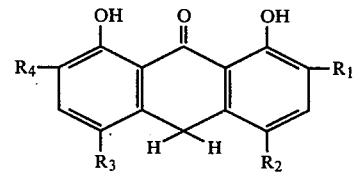

wherein $R_1$, $R_2$, $R_3$ and $R_4$, which may be identical to or different from each other, are each hydrogen, halogen, branched alkyl of 3 to 12 carbon atoms or cycloalkyl of 3 to 12 carbon atoms, provided, however, that at least one of $R_1$ to $R_4$ is other than hydrogen; the compounds are useful as dermatologics for the treatment of psoriasis, dandruff, ichthyosis and hyperkeratotic skin conditions.

9 Claims, 1 Drawing Figure

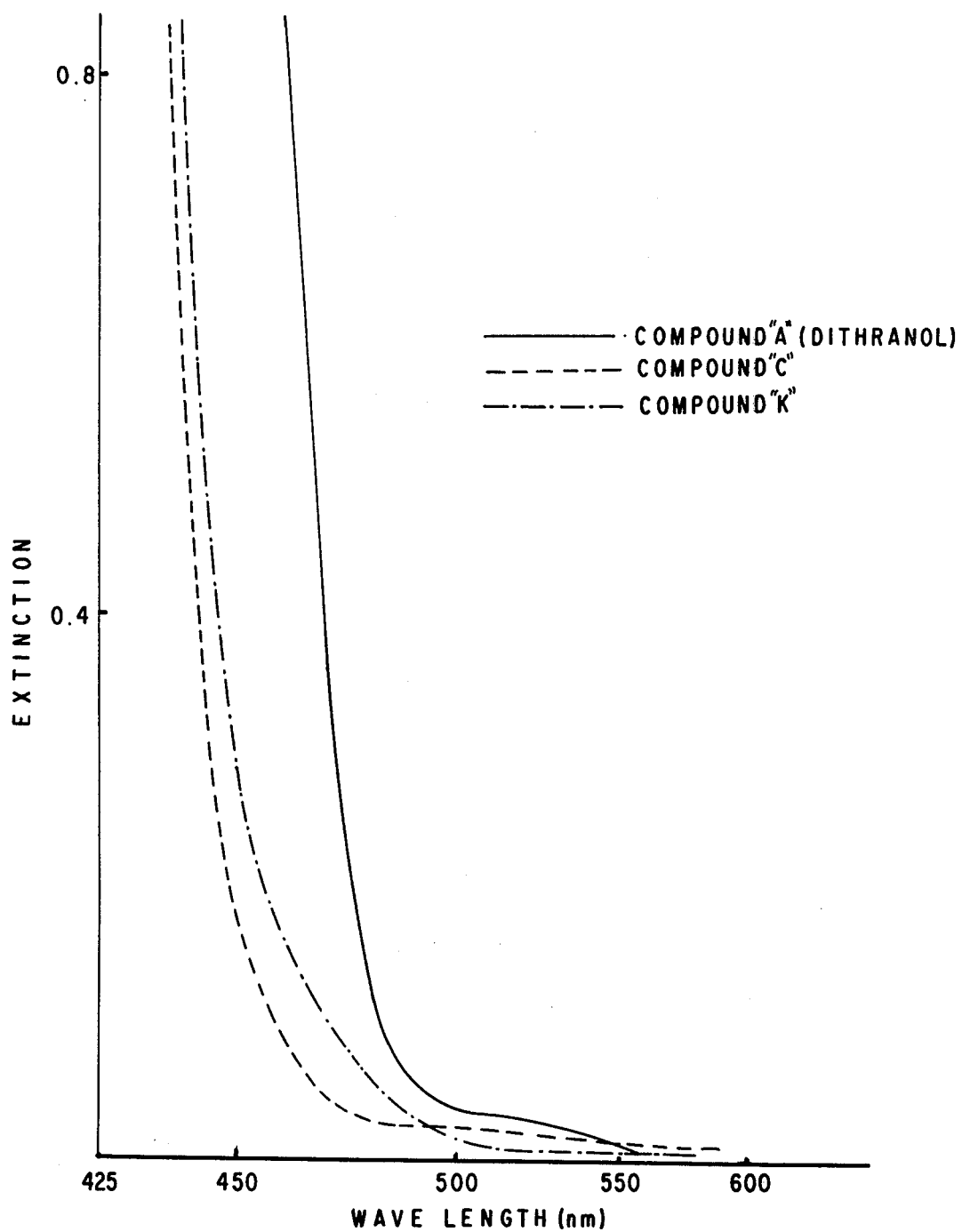

SUBSTITUTED 1,8-DIHYDROXY-9-(10H)ANTHRACENONES

This invention relates to novel substituted 1,8-dihydroxy-9-(10H)anthracenones, to methods of preparing these compounds, to pharmaceutical compositions containing them as active ingredients, and to methods of using them for the treatment of skin diseases such as psoriasis, dandruff, icthyosis and hyperkeratotic skin conditions.

More particularly, the present invention relates to a novel class of 1,8-dihydroxy-9-(10H)anthracenones represented by the formula

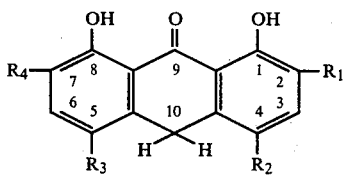

wherein $R_1$, $R_2$, $R_3$ and $R_4$, which may be identical to or different from each other, are each hydrogen, halogen, branched alkyl of 3 to 12 carbon atoms or cycloalkyl of 3 to 12 carbon atoms, provided, however, that at least one of $R_1$ to $R_4$ is other than hydrogen.

Specific examples of the halogen and hydrocarbon radicals embraced by the definition of $R_1$ to $R_4$ above are the following: Fluorine, chlorine, bromine, iodine, isopropyl, isobutyl, tert. butyl, isopentyl, neopentyl, tert. pentyl, 2-methyl-pentyl, 3-methyl-pentyl, 2,2-dimethyl-butyl, 2,3-dimethyl-butyl, 2-methyl-hexyl, 3-methyl-hexyl, 2,2-dimethyl-pentyl, 2,3-dimethyl-pentyl, 2,4-dimethyl-pentyl, 3,3-dimethyl-pentyl, 3-ethyl-pentyl, 2,2,3-trimethyl-butyl, 2-methyl-heptyl, 2,5-dimethyl-hexyl, 2-ethyl-hexyl, 2-methyl-octyl, 2-ethyl-heptyl, 2-methyl-nonyl, 2-ethyl-octyl, 2-methyl-decyl, 2-ethyl-nonyl, 2-propyl-heptyl, 2-methyl-undecyl, 2-ethyl-decyl, 2-propyl-octyl, 2-methyl-dodecyl, 2-ethyl-undecyl, 2-propyl-decyl, 2-butyl-nonyl, 2-pentyl-heptyl, cyclopropyl, cyclobutyl, cyclopentyl, cyclohexyl, cycloheptyl, cyclooctyl or cyclododecyl.

Preferred compounds of the formula I are those wherein from one to two of substituents $R_1$ to $R_4$, which may be identical to or different from each other, are each chlorine, bromine, branched alkyl of 3 to 7 carbon atoms or cycloalkyl of 3 to 7 carbon atoms, and the remainder of $R_1$ to $R_4$ are hydrogen.

Especially preferred compounds of the formula I are those wherein from one to two of substituents $R_1$ to $R_4$ are chlorine, bromine, isopropyl, tert. butyl, isopentyl, isohexyl or cyclohexyl, and the remainder of $R_1$ to $R_4$ are hydrogen.

The compounds embraced by formula I may be prepared by the following methods:

Method A

For the preparation of a compound of the formula I wherein one of substituents $R_1$ to $R_4$ is halogen, another is branched alkyl or cycloalkyl, and the remaining two are hydrogen; or from one to two of substituents $R_1$ to $R_4$ are branched alkyl or cycloalkyl, and the remainder are hydrogen, by alkylating a 1,8-dihydroxy-9-(10H)anthracenone of the formula

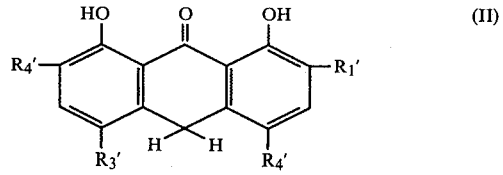

wherein $R_1'$, $R_2'$, $R_3'$ and $R_4'$ are each hydrogen, branched alkyl of 3 to 12 carbon atoms or cycloalkyl of 3 to 12 carbon atoms, provided, however, that only one of $R_1'$ to $R_4'$ is other than hydrogen, with an alkene of 3 to 12 carbon atoms, a cycloalkene of 3 to 12 carbon atoms, an alkanol of 3 to 12 carbon atoms or a cycloalkanol of 3 to 12 carbon atoms in the presence of an acid condensation agent.

The alkylation is carried out in an inert organic solvent in the presence of an acid, such as phosphoric acid, polyphosphoric acid, sulfuric acid, glacial acetic acid or phosphorous oxychloride, or in the presence of a Lewis-acid, such as anhydrous aluminum chloride, tin(II)-chloride, phosphorus pentachloride, iron (III) chloride, zinc chloride or phosphorus pentoxide.

Suitable solvents are, for example, ether, aromatic hydrocarbons such as chlorobenzene or nitrobenzene, phosphorus oxychloride, or halogenated hydrocarbons such as chloroform or ethylene chloride.

The reaction temperature is generally between 30° and 150° C.

Method B

For the preparation of a compound of the formula I wherein $R_1$ to $R_4$ are each hydrogen, halogen, branched alkyl of 3 to 12 carbon atoms or cycloalkyl of 3 to 12 carbon atoms, provided, however, that at least one of them is halogen, by halogenating a 1,8-dihydroxy-9-(10H)anthracenone of the formula II wherein $R_1'$ to $R_4'$ have the same meanings as $R_1$ to $R_4$ in formula I, provided, however, that at least one of $R_1'$ to $R_4'$ is hydrogen.

The halogenation is carried out in an inert organic solvent, for instance in an ether such as diethyl ether or dioxane, glacial acetic acid, an alcohol, a halogenated hydrocarbon such as chloroform or methylene chloride, or a mixture of any two or more of these solvents.

Examples of suitable halogenating agents are elemental halogen, sulfuryl halides or hypohalites such as sodium hypochlorite or trifluoromethyl hypochlorite.

The following examples illustrate the present invention and will enable others skilled in the art to understand it more completely. It should be understood, however, that the invention is not limited solely to the particular examples given below.

EXAMPLE 1

4,5-Dichloro-1,8-dihydroxy-9-(10H)anthracenone by method B 235 gm (3.3 mols) of chlorine were introduced into a mixture of 2.23 liters of glacial acetic acid, 1.11 liters of chloroform and 0.44 liters of ethanol at 0° to −5° C.; thereafter, 250 gm of 1,8-dihydroxy-9-(10H)anthracenone were added at 0° to −5° C., and the mixture was stirred for 20 minutes. The precipitate which had formed was collected by suction filtration, washed with petroleum ether and chloroform, and recrystallized from toluene, yielding 156 gm (48% of theory) of the compound of the formula

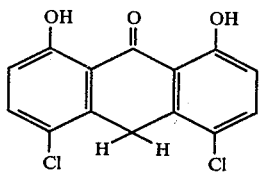

which had a melting point of 264° C.

4,5-Dibromo-1,8-dihydroxy-9-(10H)anthracenone, m.p. 239° C., was prepared in analogous manner with bromine. The yield was 62% of theory.

The following compounds were prepared in analogous manner, except that 1.5 mols of halogen were introduced into a suspension of 1.8-dihydroxy-9-(10H)anthracenone in the above-indicated solvent mixture:

4-Chloro-1,8-dihydroxy-9-(10H)anthracenone, m.p. 178° C.; yield: 32% of theory (yield of 4,5-dichloro compound: 28%).

4-Bromo-1,8-dihydroxy-9-(10H)anthracenone, m.p. 169° C.; yield: 59% of theory (yield of 4,5-dibromo compound: 20%).

When 4-tert. butyl-1,8-dihydroxy-9(10H)anthracenone was reacted in analogous manner with bromine, the following compounds were obtained:

With 1.5 mols of bromine, the main product was 4-bromo-5-tert. butyl-1,8-dihydroxy-9-(10H)anthracenone, m.p. 236°-238° C.; yield: 55% of theory.

With 3 mols of bromine, the main product was 2,4-dibromo-5-tert. butyl-1,8-dihydroxy-9-(10H)-anthracenone, m.p. 160°-162° C.; yield: 62% of theory.

With a large excess of bromine (about 8 mols), the main product was a tribromo-derivative of 4-tert. butyl-1,8-dihydroxy-9-(10H)anthracenone, m.p. 232°-234° C. The exact positions of the bromo-substituents could not be determined because of the inadequate solubility of the compound, but they are probably in the 2-, 4- and 7-positions.

EXAMPLE 2

Mixture of 2-isopropyl- and 4-isopropyl-1,8-dihydroxy-9-(10H)anthracenone by method A A solution of 56 gm of 1,8-dihydroxy-9-(10H)anthracenone in 45 ml of isopropanol and 400 ml of 105% phosphoric acid was stirred at 110° C. for 2 hours, then cooled and poured into ice water. The substrate precipitated thereby was collected by suction filtration and purified on a silicagel column (mobile phase: chloroform/heptane 1:1). 49.5 gm of a substance having a melting point of 109°-110° C. were obtained, which was found to be thin-layer chromatographically uniform; its elemental analysis corresponded to that of the values calculated for a monoisopropyl-substituted derivative of 1,8-dihydroxy-9-(10H)anthracenone. Structure elucidation with the aid of 13C NMR-spectroscopy revealed that it was a mixture consisting of 15% 2-isopropyl- and 85% 4-isopropyl-1,8-dihydroxy-9-(10H)anthracenone. The yield, based on the starting compound, was 72% of theory. The 4-isopropyl-isomer was isolated by recrystallization from n-heptane; it had a melting point of 115°-117° C.

The following compounds were prepared in analogous manner from 1,8-dihydroxy-9-(10H)anthracenone and the corresponding secndary alcohols:

4-tert. butyl-1,8-dihydroxy-9-(10H)anthracenone, m.p. 126°-127° C.;

4-isohexyl-1,8-dihydroxy-9-(10H)anthracenone, m.p. 65° C.; and 2-cyclohexyl-1,8-dihydroxy-9-(10H)anthracenone, m.p. 145°-147° C.

In these reactions dialkyl-substituted compounds, such as 2,4-dissopropyl-1,8-dihydroxy-9-(10H)-anthracenone, 2,7-diisopropyl-1,8-dihydroxy-9-(10H)-anthracenone, and 2,7-di-tert. butyl-1,8-dihydroxy-9-(10H)anthracenone are also formed as side products.

4-Bromo-5-isopropyl-1,8-dihydroxy-9-(10H)-anthracenone, m.p. 126°-130° C., was prepared in analogous manner from 4-bromo-1,8-dihydroxy-9-(10H)anthracenone and isopropanol. The reaction product also contained 25% of 4-bromo-7-isopropyl-1,8-dihydroxy-9-(10H)anthracenone.

4-Chloro-5-isopropyl-1,8-dihydroxy-9-(10H)anthracenone, m.p. 120°-123° C., was obtained from 4-chloro-1,8-dihydroxy-9-(10H)anthracenone and isopropanol.

EXAMPLE 3

2-tert. Butyl-1,8-dihydroxy-9-(10H)anthracenone by method A

About 7 gm of isobutylene were introduced into a refluxing solution of 11.3 gm of 1,8-dihydroxy-9-(10H)anthracenone in 100 ml of chloroform and 6 ml of sulfuric acid. The resulting mixture was poured into water, and the organic phase was separated and worked up as described in Example 2. 3.9 gm of 2-tert. butyl-1,8-dihydroxy-9-(10H)anthracenone, m.p. 126°-127° C., corresponding to 27% of theory, were obtained.

The following compounds were prepared in analogous manner from 1,8-dihydroxy-9-(10H)anthracenone and the corresponding alkenes:

2-Isohexyl-1,8-dihydroxy-9-(10H)anthracenone, m.p. 65° C.;

2-Cyclohexyl-1,8-dihydroxy-9-(10H)-anthracenone m.p. 145°-147° C.;

2-Isopropyl-1,8-dihydroxy-9-(10H)anthracenone, m.p. 115°-117° C.;

Mixture of 2-dodecyl- and 4-dodecyl-1,8-dihydroxy-9-(10H)anthracenone, R$_f$-value: 0.59 (Merck prepared TLC-plates 60F-254; mobile phase: toluene without chamber saturation). For comparison: R$_f$-value of 1,8-dihydroxy-9-(10H)anthracenone=0.53 (same conditions).

EXAMPLE 4

2,7-Di-tert. butyl-1,8-dihydroxy-9-(10H)anthracenone by method A

About 50 gm of isobutylene were introduced over a period of 3 hours into a stirred solution of 22.6 gm of 1,8-dihydroxy-9-(10H)anthracenone in 150 ml of glacial acetic acid, 75 ml of chloroform and 90 ml of concentrated sulfuric acid at 60° C. The resulting mixture was cooled to 5° C., and the already substantially pure substance which crystallized out was collected by suction filtration. The product contained about 5-8% of 2-tert. butyl-1,8-dihydroxy-9-(10H)anthracenone, which was removed by stirring with a mixture of equal parts of glacial acetic acid and chloroform. Yield of the 2,7-ditert. butyl-substituted compound: 35% of theory. M.p. 192° C.

The other dialkyl-substituted compounds of the present invention may be prepared in analogous manner from 1,8-dihydroxy-9-(10H)anthracenone and the corresponding alkene.

The compounds of the present invention, that is, those embraced by formula I above, have useful pharmacodynamic properties. More particularly, they are useful as dermatologics, especially for the treatment of psoriasis, dandruff, ichthyosis and hyperkeratotic skin conditions.

We have discovered that the compounds of the formula I, in comparison with the known starting compound of the formula II wherein $R_1'$ to $R_4'$ are hydrogen, exhibit special advantages with regard to their pharmacological properties. Synthetically prepared 1,8-dihydroxy-9-(10H)anthracenone (dithranol, Anthralin) which is used in the present case as the starting compound, was introduced in 1916 for the external treatment of psoriasis by Galewski. Prior thereto, since 1878, Chrysarobin was used, which was obtained by extraction from the goa-powder of the plant *Andira aroraba* L. Chrysarobin consists of a mixture of different substances, of which the most active component is considered to be 1,8-dihydroxy-3-methyl-9-(10H)anthracenone. Since the concentration of active ingredient in the goa-powder was always subject to wide variations, the introduction of synthetically prepared 1,8-dihydroxy-9-(10H)anthracenone represented significant progress in therapy. Since that time dithranol is used world-wide for the treatment of psoriasis with great success. Because of its reliable activity and the lack of systemic side-effects, dithranol is still holding its own as the standard therapeutic for the treatment of psoriasis.

There are, however, significant disadvantages in the dithranol treatment. They limit the wide ambulant use of dithranol, and therefore dithranol is mostly given to hospital in-patients. These disadvantages are:

(a) the strong, irreversible discoloration of skin and lingerie,
(b) the strong skin-irritating activity of dithranol, which is not only uncomfortable, but with careless use may also lead to an aggravation of the psoriasis (Köbner phenomenon).

Investigations relative to structure specifity of dithranol, which were carried out primarily by KREBS and SCHALTEGGER (Untersuchungen zur Strukturspezifität der Psoriasis-Heilmittel und Dithranol, Hautarzt, page 201, 1969), have shown that for antipsoriatic activity a minimal structure of the following kind is necessary:

(a) a hydroxyl group in the 1-position,
(b) a carbonyl or anthrone oxygen in the 9-position,
(c) two free hydrogen atoms in the 10-position.

If into the 2-, 3- or 4-positions an OH-group is introduced, the antipsoriatic activity disappears. From the approximately 30 compounds tested by KREBS and SCHALTEGGER, none of these compounds showed in the psoriasis treatment with regard to the therapeutic index a superior activity compared with dithranol.

1,8,9-Triacetoxyanthracene (dithranol triacetate) was introduced by HELLER and WHITEFIELD in Great Britain for the treatment of psoriasis. This compound produces less skin irritation, but it is also less active than dithranol, i.e. a real improvement of the therapeutic index could not be obtained with this compound.

Also in the article of K. K. Mustakallio, Acta Dermatovener 59, Supplementum 85, page 125 and following (1979), where 2 substituted dithranols were used, no improvement of the therapeutic index could be obtained: While bis-(formylethyl)-dithranol produced no irritation and discoloration, it also did not exhibit any antipsoriatic activity. 10-Acetyl-dithranol discolored and irritated the skin at concentrations from 0.5% even more than the starting compound.

Therefore, the object of the present invention was to overcome the disadvantages of dithranol therapy while at the same time preserving the antipsoriatic activity. The compounds, described in greater detail below, have the following significant advantages over the starting compound dithranol and the natural product chrysarobin:

1. No discoloration of the skin or lingerie,
2. Considerably less skin irritation,
3. Considerably lower toxicity,
4. Considerably better chemical stability, also upon exposure to light, which makes it possible to prepare stable pharmaceutical compositions, and
5. Less intense color, i.e. the substance itself and the compositions containing it are not so intensely yellow.

Like dithranol, the compounds inhibit the key enzymes of the carbohydrate metabolism and slow down accelerated cell divisions. These compounds are therefore useful for the treatment of skin diseases such as psoriasis, dandruff, ichthyosis and hyperkeratosis.

Thus, the known compounds 1,8-Dihydroxy-9-(10H)anthracenone (dithranol) = A
and
1,8-Dihydroxy-3-methyl-9-(10H)-anthracenone (chrysarobin) = B where tested in comparison with the novel compounds 4,5-Dichloro-1,8-dihydroxy-9-(10H)anthracenone = C
2-tert. Butyl-1,8-dihydroxy-9-(10H)anthracenone = D
2-(2-Hexyl)-1,8-dihydroxy-9-(10H)anthracenone = E
1,8-Dihydroxy-4-isopropyl-9-(10H)anthracenone = F
1,8-Dihydroxy-2,4-diisopropyl-9-(10H)anthracenone = G
4-Chloro-1,8-dihydroxy-9-(10H)anthracenone = H
2-Cyclohexyl-1,8-dihydroxy-9-(10H)anthracenone = I
2,7-Di-tert. butyl-1,8-dihydroxy-9-(10H)anthracenone = K with regard to their inhibiting effect upon enzymes, their irritating properties, their staining property of skin and lingerie, and their toxicity.

The inhibiting effect upon enzymes was determined by measurement of the inhibition of glucose-6-phosphate-dihydrogenase.

The following equilibrium was observed:

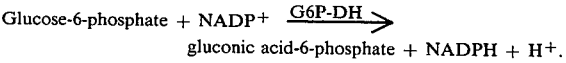

$$\text{Glucose-6-phosphate} + \text{NADP}^+ \xrightarrow{\text{G6P-DH}} \text{gluconic acid-6-phosphate} + \text{NADPH} + \text{H}^+.$$

(NADP-nicotinamide-adenine-dinucleotide-phosphate). The rate of formation of NADPH is a measure of the enzyme activity; it can be measured by means of the increase in extinction at 340, 334 or 336 nm per unit of time.

Method 0.025 ml of glucose-6-phosphate-dihydrogenase were diluted to 10 ml with distilled water (Solution I). 100 mg of nicotinamide-adenine-dinucleotide-phosphate were dissolved in 13 ml of distilled water (Solution II). 47.2 mg of glucose-6-phosphate were dissolved in another 10 ml of distilled water (Solution III). Besides this, a buffer solution (Solution IV) was prepared as follows:

0.28 gm of triethanolamine hydrochloride and 1.461 gm of ethylene-diamine tetraacetic acid disodium salt were dissolved in 1 liter of distilled water, and the solution was adjusted to pH 7.6 with sodium hydroxide. The substance to be tested was dissolved in dimethyl formamide or ethanol (Solution V). Tested end-concentrations: 25, 12.5, 6.25, 3.125, 1.56 and 0.78 µg/ml.

Determination of the inhibition of incubation

A mixture of 0.1 ml of Solution I, 0.1 ml of Solution II, 2.67 ml of Solution IV and 0.03 ml of Solution V was kept at 37° C. for 120 minutes. After addition of 0.1 ml of Solution III and thorough mixing, the change in extinction was measured photometrically at 366 nm over 3 minutes. The inhibition values were calculated from the average values of 3 measurements (as change of extinction per minute), compared to controls to which the pure solvent was added as inhibitor solution. The $ED_{50}$ was calculated according to the method of REED and MUENCH from the inhibiting values of the different concentrations. The following table contains the values thus determined:

TABLE 1

| Compound | $ED_{50}$ [µg/ml] Inhibition of incubation after 120 minutes |
|---|---|
| A | 5.60 |
| B | 6.86 |
| C | 4.63 |
| D | 6.32 |
| E | 3.61 |
| F | 5.35 |
| G | 5.67 |
| H | 3.85 |
| I | 3.94 |
| K | 7.77 |

It can be seen that the novel compounds show approximately the same, and in some cases a little better activity than the known compounds A and B.

Determination of the acute toxicity

The acute toxicity was determined in the mouse and in the rat. Determined was the $LD_{50}$, i.e. the dose after administration of which 50% of the animals died within 14 days, or it was determined how many of the 10 treated animals died within the period of observation.

The results which were obtained are summarized in Table 2.

Method of the compatibility test on guinea pigs

Guinea pigs of the Perbright White strain, with a body weight of about 350 gm, were fed with standard guinea pig feed (Altromin 3022) and water ad lib.

During the test, the animals were kept in single cages. The test substances, which were dissolved in a well compatible solvent, were applied to the skin of the animals (diameter of the test area 3.5 cm) daily for 3 weeks, from Monday to Friday. The animals were shaved each Monday, Wednesday and Friday in the early morning, the treatment with the test substances was performed in the early afternoon. Immediately before administration of the substance, the skin reaction was tested. The evaluation was carried out visually, and erythema, edema, and mycosis of the skin were considered.

The following evaluation was made:
0: no irritation
0.5: weak erythema
1: distinct erythema
2: strong erythema with beginning edema
3: very strong erythema with edema or beginning necrosis.

The numerical sum of the reactions was used for the total evaluation of a group of animals.

The sensitizing activity was tested 2 weeks after the skin compatibility test with 1:10 to 1:50 of the originally used concentrations behind the ears. The results are shown in Table 3.

TABLE 3

| Compound | Concentration % | Number of animals | Sum of the reactions divided by the number of animals at the end of the | | |
|---|---|---|---|---|---|
| | | | 1st | 2nd | 3rd week |
| A | 0.015 | 6 | 0.66 | 0.33 | 0.33 |
| | 0.03 | 12 | 1.3 | 2.16 | 2.25 |
| C | 0.03 | 12 | 0 | 0 | 0.04 |
| | 0.045 | 6 | 0.166 | 0.66 | 0.41 |
| D | 0.03 | 12 | 0.083 | 0.042 | 0.00 |
| F | 0.015 | 6 | 0.085 | 0.085 | 0.085 |
| | 0.045 | 6 | 0.085 | 0.085 | 0.085 |
| K | 0.03 | 12 | 0.00 | 0.042 | 0.00 |

It can be seen that the novel compounds C, F, D and K are considerably more skin-compatible than compound A. 0.03% of compound A sensitized 3 out of 12 animals. Compounds C, D, F and K produced no sensitization.

Orienting skin compatibility in humans

Method

TABLE 2

| | | Compound A | | | Compound F | | | Compound C | | Compound K | |
|---|---|---|---|---|---|---|---|---|---|---|---|
| Animal | Route of Administration | $LD_{50}$ mg/kg | Dose mg/kg | Number of dead animals | $LD_{50}$ mg/kg | Dose mg/kg | Number of dead animals | Dose mg/kg | Number of dead animals | Dose mg/kg | Number of dead animals |
| Mouse | i.p. | 2.42 | — | — | 52 | — | — | 2000 | 1/10 | 1000 | 0/10 |
| Mouse | sc. | 2.22 | — | — | — | 2000 | 0/10 | 2000 | 6/10 | 1000 | 0/10 |
| Mouse | p.o. | — | 2000 | 2/10 | — | 2000 | 0/10 | 2000 | 0/10 | 4000 | 0/10 |
| Rat | i.p. | 5.19 | — | — | 45 | — | — | 2000 | 0/10 | | |
| Rat | sc. | — | 1000 | 2/10 | — | 2000 | 0/10 | 2000 | 0/10 | | |
| Rat | p.o. | — | 2000 | 1/10 | — | 2000 | 0/10 | 2000 | 0/10 | | |

The skin compatibility tests were carried out on guinea pigs, and for orientation purposes on humans.

Ointments, each containing individually 0.44% of compounds A, C, D, E, F, G and K were applied to the forearms of volunteer human test subjects, covered with bandage gauze and allowed to remain on the skin for 16 hours. After 16 hours the ointments were washed off with soap solution, and the skin irritation and discoloration, if any, were evaluated visually and photographed. Then, the test ointments were again administered and allowed to remain on the skin until the next day. Again, the reactions were evaluated and a new treatment was started. After 3 days (3 applications) the concentration of active ingredient in those preparations which showed no reaction was doubled to 0.88%, and the treatment was continued for another 2 days.

Results

While dithranol (Compound A) produced a strong skin irritation with erythema and a brownish-violet discoloration after only the second application, the ointments with compounds C, D, E, F and G produced no skin irritation or discoloration of the skin. The bandage gauze with which the area of treatment was covered, was irreversibly discolored violet in the test with compound A, whereas no discoloration could be noticed in the tests with compounds C, D, E, F, G and K. The skin area treated with compound A peeled after about one week, whereas in the treatments with other substances no changes of the skin could be determined.

Compound B produced a skin discoloration similar to compound A, as the application of a 0.44% ointment showed.

In a further test, according to the method of Mustakallio, compound A was applied at concentrations of 1, 2, 4, 8, 16, 32 mmols in white vaseline and allowed to remain on the skin for 4 hours under occlusion. Compounds C and K, however, were applied at concentrations of 4, 8, 16, 32, 64, 128 mmols, also in white vaseline, and allowed to remain on the skin for 16 hours under occlusion. While compound A produced discoloration and skin irritations after 4 hours of occlusion at concentrations of 2 mmols or more and after 16 hours at concentrations of 1 mmol or more, no skin irritations or discolorations could be observed in the tests of compounds C and K, not even at the highest concentrations after 4 and after 16 hours. This means that the novel compounds are more compatible by a factor of at least 64.

Penetration and metabolization in the skin

Penetration tests carried out in vitro on the skin of pigs (this skin was used due to its morphological structure and pilosity, which is relatively similar to the human skin) showed by means of thin-layer chromatography that compounds A, C, G and K penetrate to an approximately equal extent from the same carriers to the different layers of the skin, and that they are metabolized in a similar manner.

This proves that the significantly better skin compatibility of the compounds according to the invention is not due to poorer penetration.

Natural color of the substance

Topically administrable substances which are colored are undesirable for cosmetic reasons and also because the lingerie may become soiled. FIG. 1 of the attached drawing shows that the compounds C and K in the shortwave portion of visible light (beginning at 380 nm) show significantly less UV-absorption, i.e. their yellow color is diminished. This is also expressed by the optic impression of the preparations. As, furthermore, no discoloration occurs, slight soilings of lingerie can easily be removed, as tests with lingerie showed. This is a further advantage compared with dithranol.

Photostability and photosensitivity

Since antipsoriatics are also applied to skin areas exposed to light, the stability under light exposure was tested; particularly, the dihalogenated derivatives, where the formation of radicals is possible under the influence of light exposure, were tested.

Stability under light irradiation

Compound C and dithranol (A) in solution (toluene or xylene) were exposed for 30 minutes to a 400 W high-pressure mercury vapor lamp (Type HPM 12, Phillips), where the spectrum of light emission was changed by adding heavy metal salts. While dithranol under these conditions is nearly completely decomposed, no decomposition could be determined for compound C in the thin-layer chromatogram. Moreover, no chlorination of toluene could be found gas-chromatographically, which would point to radical formation (sensitivity 0.0001%).

Photo-sensitization

Since some halogenated aromatic substances have a photo-sensitizing activity, the photo-sensitization of compound C was also tested in vivo on the guinea pig.

Method

Guinea pigs were treated for 3 weeks on 5 week-days with a 0.01% alcoholic solution of compound C. After 30 minutes each animal was exposed for 10 minutes to a 125 W mercury high-pressure lamp (ultra violet sun lamp). The irradiation was carried out in such a way that no UV-B erythema appeared.

No photo-sensitizing activity could be determined.

For pharmaceutical purposes the compounds of the present invention are topically administered to a warm-blooded animal in need of dermatological treatment as active ingredients in customary topical compositions consisting essentially of an inert pharmaceutical carrier and an effective concentration of the active ingredient, such as ointments, gels, creams, tinctures and the like. The effective concentration of the compounds of the present invention in such topical compositions is from 0.01 to 5%, preferably 0.1 to 1%, by weight based on the total weight of the composition.

The following examples illustrate a few topical pharmaceutical compositions comprising a compound of the present invention as an active ingredient and represent the best modes contemplated of practicing the invention. The parts are parts by weight unless otherwise specified.

EXAMPLE 5

Ointment

The ointment is compounded from the following ingredients:

| | |
|---|---|
| 4,5-Dichloro-1,8-dihydroxy-9-(10H)anthracenone | 0.5 parts |
| tert. Butyl-hydroxy-anisole | 0.3 parts |
| Salicylic acid | 1.0 parts |
| Cetyl alcohol | 10.0 parts |
| Viscous paraffin oil | 45.0 parts |
| White vaseline | 43.2 parts |

-continued

| | Total | 100.0 parts |

Preparation

The ingredients are combined, the mixture is heated to 70° C. while stirring, and stirring is continued until the temperature of the mixture dropped to 40° C. The resulting ointment contains 0.5% by weight of the active ingredient.

EXAMPLE 6

Gel

The gel is compounded from the following ingredients:

| 4,5-Dichloro-1,8-dihydroxy-9- | | |
| (10H)anthracenone | | 0.5 parts |
| Yellow vaseline | | 78.5 parts |
| Viscous paraffin oil | | 21.0 parts |
| | Total | 100.0 parts |

The gel is prepared in analogy to the ointment of Example 5. The concentration of active ingredient is also 0.5% by weight.

EXAMPLE 7

Lipo-gel

The gel is compounded from the following ingredients:

| 4,5-Dichloro-1,8-dihydroxy-9- | | |
| (10H)anthracenone | | 0.5 parts |
| Propane-1,2-diol fatty acid | | |
| esters of medium chain | | |
| length (Miglyxol 840) | | 82.5 parts |
| Hydrogenated castor oil | | 15.0 parts |
| Triethyl citrate | | 2.0 parts |
| | Total | 100.0 parts |

The gel is prepared in analogy to the ointment of Example 5. The concentration of active ingredient is also 0.5% by weight.

EXAMPLE 8

Cream

The cream is compounded from the following ingredients:

| 4,5-Dichloro-1,8-dihydroxy- | | |
| 9-(10H)anthracenone | | 0.2 parts |
| Cetyl stearyl alcohol | | 12.8 parts |
| Propane-1,2-diol fatty acid | | |
| esters of medium chain | | |
| length (Miglyol 840) | | 25.0 parts |
| Cremophor O (acyl-substituted | | |
| polyaddition product of | | |
| cetyl stearyl alcohol with | | |
| 20 to 25 mols of ethylene | | |
| oxide) | | 3.0 parts |
| Span 40 (sorbitan monopalmitate) | | 3.0 parts |
| Distilled water | | 56.0 parts |
| | Total | 100.0 parts |

Preparation

The Span 40, the Cremophor O, the Miglyol 840 and the cetyl stearate alcohol are combined, the mixture is melted at 75° C. and held at this temperature while the active ingredient is stirred in, and the boiled distilled water is added at 75° C. The resulting composition is filled into suitable containers and allowed to cool. The cream contains 0.2% by weight of the active ingredient.

EXAMPLE 9

Fatty cream

The cream is compounded from the following ingredients:

| 4,5-Dichloro-1,8-Dihydroxy-9- | | |
| (10H)anthracenone | | 0.2 parts |
| Propane-1,2-diol fatty acid | | |
| esters of medium chain length | | |
| (Miglyol 840) | | 20.8 parts |
| Non-ionic emulsifier | | 7.0 parts |
| Sorbitan sesquioleate | | 7.0 parts |
| Miglyol gel | | 15.0 parts |
| Water | | 50.0 parts |
| | Total | 100.0 parts |

The cream is prepared in analogy to the cream of Example 8. The active ingredient content is also 0.2% by weight.

Any one of the other compounds embraced by formula I may be substituted for the particular active ingredient in Examples 5 through 9. Likewise, the concentration of active ingredient in these illustrative examples may be varied to achieve the range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

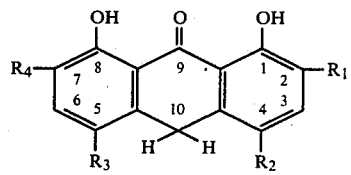

wherein $R_1$, $R_2$, $R_3$ and $R_4$ are each hydrogen, halogen, branched alkyl of 3 to 12 carbon atoms or cycloalkyl of 3 to 12 carbon atoms, provided, however, that at least one of $R_1$ to $R_4$ is other than hydrogen.

2. A compound of claim 1, where from one to two substituents $R_1$ to $R_4$ are each chlorine, bromine, branched alkyl of 3 to 7 carbon atoms or cycloalkyl of 5 to 7 carbon atoms, and the remainder of $R_1$ to $R_4$ are hydrogen.

3. A compound of claim 1, where from one to two of substituents $R_1$ to $R_4$ are each chlorine, bromine, isopropyl, tert. butyl, isopentyl, isohexyl or cyclohexyl, and the remainder of $R_1$ to $R_4$ are hydrogen.

4. The compound of claim 1 which is 4,5-dichloro-1,8-dihydroxy-9-(10H)anthracenone.

5. The compound of claim 1 which is 2-tert. butyl-1,8-dihydroxy-9-(10H)anthracenone.

6. The compound of claim 1 which is 2,7-di-tert. butyl-1,8-dihydroxy-9-(10H)anthracenone.

7. The compound of claim 1 which is 4-isopropyl-1,8-dihydroxy-9-(10H)anthracenone.

8. A topical dermatologic pharmaceutical composition consisting essentially of an inert pharmaceutical carrier and an effective dermatologic amount of a compound of claim 1.

9. The method of alleviating psoriasis, dandruff, ichthyosis or hyperkeratotic skin conditions in a warm-blooded animal, which comprises topically applying to the affected skin areas of said animal an effective amount of a composition of claim 8.

* * * * *

UNITED STATES PATENT AND TRADEMARK OFFICE
CERTIFICATE OF CORRECTION

PATENT NO. : 4,327,114
DATED : April 27, 1982
INVENTOR(S) : ROLF BRICKL and HANS EBERHARDT It is certified that error appears in the above—identified patent and that said Letters Patent is hereby corrected as shown below:

Column 3, line 52: "substrate" should read -- substance --.

Column 4, line 3: "secndary" should read -- secondary --.

Column 4, line 11: "2,4-dissopropyl" should read

-- 2,4-diisopropyl --.

Signed and Sealed this

Third Day of August 1982

[SEAL]

Attest:

GERALD J. MOSSINGHOFF

Attesting Officer     Commissioner of Patents and Trademarks